(12) United States Patent
Alsuhaibani

(10) Patent No.: US 11,202,865 B2
(45) Date of Patent: Dec. 21, 2021

(54) SYRINGE FOR ONE-HANDED INJECTION AND ASPIRATION

(71) Applicant: SUBUL ALKHEBRAH INDUSTRIAL COMPANY, Riyadh (SA)

(72) Inventor: Abdulaziz A. Alsuhaibani, Riyadh (SA)

(73) Assignee: SUBUL ALKHEBRAH INDUSTRIAL COMPANY, Riyadh (SA)

(*) Notice: Subject to any disclaimer, the term of this patent is extended or adjusted under 35 U.S.C. 154(b) by 0 days.

(21) Appl. No.: 16/754,835

(22) PCT Filed: Jul. 11, 2019

(86) PCT No.: PCT/IB2019/055927
§ 371 (c)(1),
(2) Date: Apr. 9, 2020

(87) PCT Pub. No.: WO2020/012410
PCT Pub. Date: Jan. 16, 2020

(65) Prior Publication Data
US 2020/0405962 A1 Dec. 31, 2020

(30) Foreign Application Priority Data
Jul. 11, 2018 (SA) .................. 118390710

(51) Int. Cl.
*A61M 5/31* (2006.01)
*A61M 5/315* (2006.01)

(52) U.S. Cl.
CPC ........ *A61M 5/3137* (2013.01); *A61M 5/3148* (2013.01); *A61M 5/31511* (2013.01)

(58) Field of Classification Search
CPC .............. A61M 5/3137; A61M 5/3148; A61M 5/31511; A61M 5/315; A61M 5/31;
(Continued)

(56) References Cited

U.S. PATENT DOCUMENTS 1,221,103 A    4/1917  Sorensen
2,972,991 A *  2/1961  Burke .................. A61M 5/178
                                                604/110
(Continued)

FOREIGN PATENT DOCUMENTS

DE   20 2012 006 191 U1   8/2012
JP        2000-296178 A  10/2000
(Continued)

OTHER PUBLICATIONS

International Search Report and Written Opinion dated Dec. 16, 2019 for PCT/IB2019/055927 filed on Jul. 11, 2019, 6 pages.
(Continued)

*Primary Examiner* — Brandy S Lee
*Assistant Examiner* — Hong-Van N Trinh
(74) *Attorney, Agent, or Firm* — Xsensus LLP

(57) ABSTRACT

A single-handed syringe may be used in injection and in aspiration for stable and consistent single-handed use. The syringe includes a hollow cylinder body, which has a front tip that the aspirated materials pass through toward/from a cylinder cavity. A rear plunger handle and a front plunger handle, in combination with a straight external prominence formed longitudinally along an outer surface of the cylinder body permits ease, accuracy, and precision of plunger movement during aspiration and injection functions.

11 Claims, 5 Drawing Sheets

(58) Field of Classification Search
CPC ........ A61M 2005/3139; A61M 5/3129; A61M 2205/586
See application file for complete search history.

(56) References Cited

U.S. PATENT DOCUMENTS

| | | | |
|---|---|---|---|
| 3,325,061 A | 6/1967 | Ellsworth | |
| 3,990,446 A | 11/1976 | Taylor | |
| 4,263,911 A | 4/1981 | McCormack et al. | |
| 4,484,915 A | 11/1984 | Tartaglia | |
| 4,639,248 A * | 1/1987 | Schweblin | A61B 10/0045 422/923 |
| 4,813,433 A | 3/1989 | Downey | |
| 5,135,511 A | 8/1992 | Houghton et al. | |
| 5,582,595 A | 12/1996 | Haber et al. | |
| 5,814,023 A | 9/1998 | Fulk et al. | |
| 5,833,668 A | 11/1998 | Aguilar | |
| 6,231,550 B1 | 5/2001 | Laughlin | |
| 6,962,576 B2 | 11/2005 | Sibbitt | |
| 2004/0073172 A1 | 4/2004 | Acha Gandarias | |
| 2005/0192543 A1 | 9/2005 | Sibbitt | |
| 2005/0215956 A1 | 9/2005 | Nerney | |
| 2006/0258990 A1 | 11/2006 | Weber | |
| 2011/0046604 A1 | 2/2011 | Felsovalyi et al. | |
| 2011/0166531 A1 | 7/2011 | Stroumpoulis et al. | |
| 2013/0131606 A1 | 5/2013 | Bertocci | |
| 2014/0296868 A1 | 10/2014 | Garrison et al. | |
| 2015/0297457 A1 | 10/2015 | Buder et al. | |

FOREIGN PATENT DOCUMENTS

| | | |
|---|---|---|
| JP | 2014-30559 A | 2/2014 |
| SA | 6721 B | 12/2019 |
| WO | 2011/137437 A2 | 11/2011 |

OTHER PUBLICATIONS

Decision to Grant, Saudi Arabian Application No. 118390710, filed Jul. 11, 2018 with English translation.
Extended European Search Report dated Sep. 23, 2020 in European Application No. 19833797.4.

* cited by examiner

SYRINGE FOR ONE-HANDED INJECTION AND ASPIRATION

CROSS-REFERENCE TO RELATED APPLICATIONS

The present application is based on PCT filing PCT/IB2019/055927, filed Jul. 11, 2019, which claims priority to SA 118390710, filed Jul. 11, 2018, the entire contents of each are incorporated herein by reference.

TECHNICAL FIELD

The present disclosure generally relates to the field of medical devices, especially syringes that may be used in aspiration and injection modes of operation. More particularly, the syringe is valuable in different fields, including medical, agricultural, industrial, and personal use.

BACKGROUND ART

Various conventional syringes are discussed below.

Specialty syringes, such as that described in U.S. Pat. No. 4,484,915, have been made with multiple axially extending members that attach to a movable flange disposed at a forward end of the syringe. The flange is formed with a circular opening into which a syringe body is inserted, which allows the fingers of the user to apply a backward force (away from the forward end of the syringe) that is mechanically translated to the plunger. A fixed flange is fixedly included at the back end of the cylinder so the user may place their thumb on the fixed flange to provide an oppositely oriented force to the force applied by the users fingers on the movable flange during an aspiration operation. During the aspiration operation, the movable flange is moved toward the fixed flange, and the multiple axial extending members move along an outer surface of the syringe.

U.S. Pat. No. 1,221,103 describes a process that uses a plunger that moves inside the cylinder cavity. The plunger has two arms outside the cylinder with two handles at their front end for forefingers application, and a prominent part at the rear end of the cylinder to put the thumb over it while aspirating the sample.

U.S. Pat. No. 4,639,428 describes a syringe with one-handed samples aspiration and injection. The syringe has one rod plunger which is designed to be one-half of a cylinder moving through the hollow cylinder. This design has a semi sealed cylinder at its rear end; where the plunger will pass through it, as this will prevent plunger removal or introduction to the cylinder in the process of assembly during manufacturing.

German Pat. No. DE202012006191 describes a one-hand operated syringe with a plunger that has two arms that move outside the barrel and adhere to its body. The arms are connected to the plunger's handle. The pushing plunger rod is cylindrical in shape and moves inside the cylindrical cavity.

U.S. Pat. No. 3,316,909 shows how samples are aspirated and injected by a device with a hand grip. The device operates by a user placing the thumb inside the ring at the rear end of the plunger rod, and then pulling it back to aspirate or moving it forward to aspirate.

U.S. Pat. No. 20040073172 describes a structure with longitudinal grooves in a cylinder wall to make the plunger's body pass through the grooves.

U.S. Pat. Nos. 3,990,446, 5,135,511, and 5,582,595 describe devices with an extension added to the rear end of the cylinder, which helps in pulling the plunger backward using a one-hand technique.

U.S. Pat. No. 3,990,446 uses a seal in the process of drag and injection with one hand. A rod extends from the cylinder back along the piston from the outside.

U.S. Pat. No. 3,325,061 describes a structure with an added arm at one of the cylinder sides, passing through a dedicated passage in the cylinder handle and it is connected to the plunger handle with a dedicated groove. This movement of the arm occurs by forcing a finger in a designated area, which has rough surface to reduce the possibility of finger slippage.

SUMMARY

The present inventor identified several suboptimal features about conventional syringes used for both injection and aspiration, as well as adapters that assist in aspiration. First, the inventor recognized that in conventional injection mode, users normally clamp the barrel of the syringe between the user's index finger and the middle finger, while depressing the plunger with the users thumb. However, a different gripping action is used for aspiration. Typically, aspiration is performed with two hands, one holding the body of the syringe, while the other grips the end of the plunger and withdraws the plunger from the body of the syringe. Two-handed operation is not ideal because the user may very well want to use the other hand for another task, such as holding a bottle from with the liquid is withdrawn. While devices such as that described above in U.S. Pat. No. 4,484,915 allow for a one-handed aspiration operation, it does so by integrating a complex three part structure with a syringe, and prevents a user from conveniently using a single configuration for both injection and aspiration. Moreover, the multiple axial extending members move along an outer surface of the syringe which makes it difficult for the user to position their index and middle fingers in normal positions about the syringe barrel because the multiple axial extending members can too easily rub against one, or both, of the users fingers. Thus, during an aspiration operation the second flange is added with the axially extending members to support a dedicated aspiration operation.

With regard to the device in U.S. Pat. No. 1,221,103 the present inventor recognized that syringe external plunger arms are unsupported, and the internal plunger arm is in the middle, which might cause the user's thumb to slide away from the handle especially in small-sized injections, making its safety questionable.

With regard to the device in U.S. Pat. No. 4,639,428 the present inventor recognized that the manufacturing process and syringe assembly will be more difficult with the presence of the ring around the cylinders body which keeps the external plunger arm around the cylinder's body, and semi sealed cylinders rear end as well. Furthermore, a prominence along with the plunger's handles; might provide discomfort to one or more of the operator fingers.

With regard to the device in German Pat. No. DE202012006191 the present inventor recognized that the outer arms lack stabilizing members to make their movement steady and prevent them from moving away from cylinder body. Also, the internal cylindrical plunger rod will be adherent into the inner surface of the cylindrical wall, which will make the aspiration unsafe as it interferes with the thumb while aspirating. Furthermore, a thumb or finger could slip over the cylinders handle.

With regard to the device in U.S. Pat. No. 3,316,909 the present inventor recognized that this syringe will not be precise enough to a user who is seeking to extract a precise amount of sample size during aspiration. In addition, needle stability might be compromised during aspiration process, which, in turn, will cause problems such as hemorrhage, for example.

With regard to the device in U.S. Pat. No. 20040073172 the present inventor recognized that the structure will cause syringe capacity to be reduced in half, which, in turn, will make the syringe dimensions almost double if compared to the current syringes with same size.

With regard to the devices in U.S. Pat. Nos. 3,990,446, 5,135,511 and the U.S. Pat. No. 5,582,595 the present inventor recognized that the design will make the syringe length double conventional length, and especially difficult to use in small spaces.

With regard to the device in U.S. Pat. No. 3,990,446 the present inventor recognized that during withdrawal of the plunger, the length of the syringe will nearly double because of the presence of that rod. Thus, this structure limits its applicability in critical situations and narrow places because of its elongated structure.

With regard to the device in U.S. Pat. No. 3,325,061 the present inventor recognized that the structure does not tolerate strong movements and it will require the other hand to balance the needle while aspirating or injecting the samples.

In light of the limitations with the above-described devices, the presently disclosed device is a syringe that allows for comfortable, precise single-handed injection and aspiration. The structure of the syringe has been configured to allow operation by one-hand for injecting samples by pushing the plunger inside the cylinder cavity and aspirating the samples by pulling the same plunger using digits on one hand. In turn, this frees the other hand to be used for other medical steps such as fixing a patient's skin or stabilizing the needle while injecting or aspirating.

As will be described, the syringe is composed of a hollow cylinder having two ends: front (anterior) one which ends with the tip of the syringe and configured to receive a needle or tube or aspirate samples directly through it, and rear (posterior) end, which is open to allow the seal and internal plunger arms to pass through the cylinder's cavity. The internal plunger's arm is configured to cover the one-half of internal cylinder surface, which provides space to accommodate the users thumb during aspiration process when it is put over the rear surface of cylinder's handle. External plunger arms are moving adherent and parallel to the outer surface of cylinder's wall, the forward end of the external arms have handle(s) that allow the user to withdraw the plunger when the forefinger(s) are applied over their anterior surface and urge it toward the cylinders rear end, while the thumb is applied at the cylinder handle's posterior surface, and by bringing the users fingers toward each other, the plunger will move backward with the seal and the sample will be aspirated into syringe cavity through the syringe tip. The injection process will be started by applying the thumb over the posterior surface of the rear plungers handle and the forefinger(s) over the anterior surface of the cylinder handle and by bringing these fingers toward each other the plunger will move forward with the seal and the sample will be injected through the syringe tip with the digits on the same hand.

A longitudinal prominence over the external cylinder body is added to make the plunger movement straight while injecting or aspirating. This prominence (e.g., as in FIG. 5) has two curved surfaces to keep the external arms adherent to the external surface of cylinder while the arms are moving.

The syringe structure described herein uses minimal components that are combined in a particular way to provide a safe and easy injection and aspiration with a one-hand technique. The device increases the accuracy of aspirated sample volume, as well as maintain consistent physical at the location of the sample place, such as when accessing a deep vein. In addition, the structure reduces the risks and complications of using both hands in emergency situations, i.e. bleeding due to multiple punctures to the vessels; and this is a critical in severely injured patients, especially when accessing deep veins.

Other than in the medical field, this syringe is also useful to laboratory technicians when aspirating samples from test tubes and is a convenient replacement to a bulb syringe for doing so. It also allows for easy aspiration of syrup medications from bottles by enabling the user to hold the bottle in one hand and the syringe with the other. For instance, mothers who are administering medicines to their child.

BRIEF DESCRIPTION OF DRAWINGS

The features, aspects, and advantages of invention will become apparent from the following description, appended claims and accompanying exemplary embodiments shown in the drawings which includes the following drawings for embodiments, Models (A) and (B), as follows:

DESCRIPTION OF EMBODIMENTS

For a first embodiment, "Model (A)" is described with reference to FIGS. 1, 2 & 3 and include the following components: [102], [103], [104], [105], [106], [107], [108], [109] and [110] are all associated with a cylinder, and components: [111], [112], [113], [114], [115], [116], [117], [118], [119], [120], [121] and [122] are all associated with a plunger.

Figure 1:
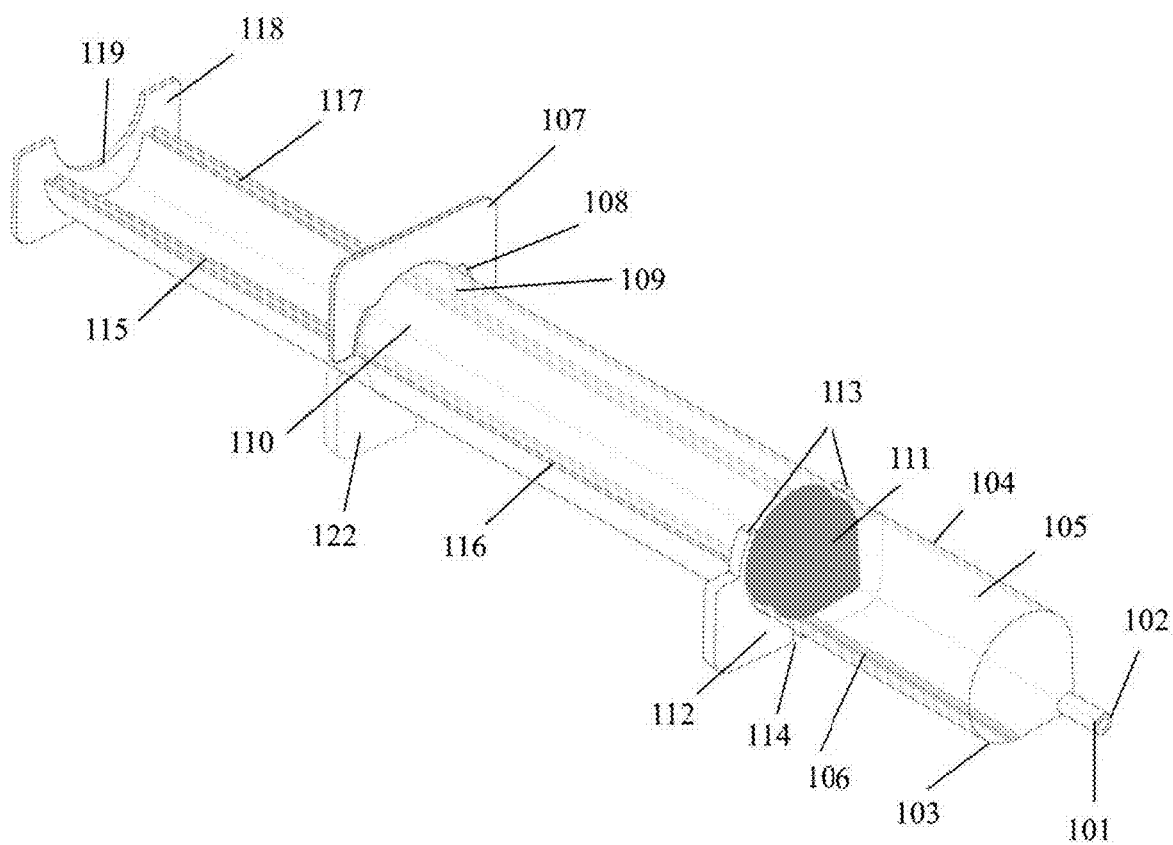
FIG. 1 is a perspective view of a syringe for one-handed injection and aspiration according to an embodiment, Model (A)

FIG. 1 shows a hollow cylinder body [104] with a conically shaped front (anterior) end [103] which ends with a frontal syringe tip (or frontal tip) [102] that is equipped to have needles or tubes attached thereto. The hollow cylinder body's [104] rear (posterior) end [110] is open to allow the seal [111] and internal plungers arm [115] to pass therethrough to an internal opening (or cavity) [105] of the hollow cylinder body [104]. A cylinder handle [107] is disposed at a rear (posterior) cylinder end, and includes two cylinder handle grooves (or spaces) [108] close to an outer wall of the hollow cylindrical body [104] to allow wings [113] of a front plunger handle [112] to pass therethrough during assembly of one-handed syringe or when removing the plunger body from the hollow cylinder body [104]. A straight external prominence [106] (also described as a straight longitudinal prominence) is formed as a protruding spine along the external surface of the hollow cylinder body [104] and is sized to straddle a space [114] formed between parts of the front plunger handle [112]. As best seen in FIG. 2, external plunger arms [116] have an arcuate shape that match and abut an outer surface of the hollow cylinder body [104]. Similarly, an inner plunger arm [115] has an arcuate shape that matches and abuts an inner surface of the hollow cylinder body [104] such that when viewed in cross section, the hollow cylinder body [104] is sandwiched between the external plunger arms [116] and internal plunger arm [115]. The combination of the sandwiched structure 116/104/115 and the fitting of the space [114] over the straight external prominence [106] allow a movement of the plunger in/out of the hollow syringe body to be straight, without a spiraling, or rotation.

As the plunger is being extracted to a near maximum amount, where the seal [111] is nearly extracted from the hollow cylinder body, a movement of the plunger will be stopped by the internal prominence [109] from cylinder body [104], which is disposed at the rear of hollow cylinder body [104]. This internal prominence [109] serves to prevent an accidental complete removal of the plunger, and seal [111], during an aspiration operation.

Except for the syringe seal [111], which is made of rubber, such as synthetic rubber, the syringe parts are made from plastic, such as polypropylene for the hollow cylinder body [104], and polyethene for the plunger and handles. While the present embodiment uses parts made from plastic and synthetic rubber, other materials may be used as well, such glass and stainless steel barrels and/or plungers.

The seal [111] is sized to press-fit radially against the inner wall of the hollow cylinder body [104] so as to prevent a fluid sample from leaking around the seal during injection or aspiration. A rear surface of the seal [111] is connected to the internal plunger arm [115] which has an arcuate shape, and extends from between 20% to 80% around the hollow cylinder body, although the internal plunger arm [115] extends around 50% of the body in this embodiment. Likewise, the outer plunger arm [116] is arcuate and extends from between 20% and 80%, although the extension is 50% in this embodiment. A rear end of internal plunger arm [115] is connected to an anterior surface of the rear (posterior) plunger handle [118] which, also, is connected to the rear end [117] of external plunger arms [116]. The rear (posterior) plunger handle [118] is diametrically opposite to the cylinder handle [107] when viewed in cross section and has a notch [119] shaped similar to the internal arm curvature.

During assembly, the external plunger arms [116] are assembled on a same side of cylinder body [104] where the straight longitudinal prominence [106] is positioned, thus allowing the external plunger arms [116] to pass into the space between the plunger arms and handles [114]. Inner surfaces of the external plunger arms [116] oppose the outer surface of cylinder body [104] and slide axially along the outer surface of the cylinder body [104] during movement of the plunger. There is a gap [117] between the external and internal arms that is similar to the cylinders body [104] thickness, which allows passage of cylinder body [104] between internal and external arms of the plunger. A front end of the external plunger arms [116] abuts a rear surface of front plunger handle [112] which is configured to be at a same longitudinal depth as the seal [111]. The front plunger handle [112] has wings [113] that at least extend partially around the outer surface of cylinder body [104] to maintain a movement of the external arm [116] against the outer surface of the hollow cylinder body [104] and to prevent it from deviating away from the hollow cylinder body [104].

An additional plunger handle [122] is optionally included about a rearward position of the outer surface of the external plunger arms [116]. The additional plunger handle [122] has a similar shape as the front plunger handle [112] but positioned further back than the front plunger handle [112]. The additional plunger handle [122] may be particularly useful if the syringe is large; i.e. larger than a comfortable finger span for a user. In use, the front plunger handle [112] and the additional plunger handle [122] are used by the user in a two-step aspiration (or injection) process to withdraw the plunger by a larger amount that is comfortable for a finger span of the user. To aspirate, in a first step, it starts by placing the user's forefingers (index and middle fingers for example) on a forward surface of the additional plunger handle [122] and thumb on the cylinder handle [107]. When the user pinches thumb and other forefingers together, the pinching force urges the plunger backwards by a first amount. Subsequently, in a second step, the user moves his or her forefingers to a front surface of the front plunger handle [112], then pinches thumb and forefingers together for a second time, and thus further withdraws the plunger from the cylinder, thus aspirating an even larger amount of sample. An injection process is straight forward, with the user grasping the hollow cylindrical body 104 between his or her forefingers, often with the pointer finger on the front surface of the cylinders cylinder handle 107. Then, the user places their thumb on the rear plunger handle, and pinches their thumb and forefingers together to urge the plunger forward through the hollow cylinder body 104, and expelling the sample held in the hollow cylinder body 104 through the frontal tip 102.

In this embodiment, the front plunger handle [112], external plunger arms [116], rear (posterior) plunger handle [118], internal plunger arm [115] and straight external prominence [106] are located on one longitudinal side of the syringe, while the cylinder handle [107] is located in the other side. Other embodiments include repositioning of some or all of these components to other areas about the syringe. For example, the straight external prominence, and associated space [114] may be located around a side of syringe. Similarly, more than one prominence, space and wings may be used for added stability.

Figure 2:
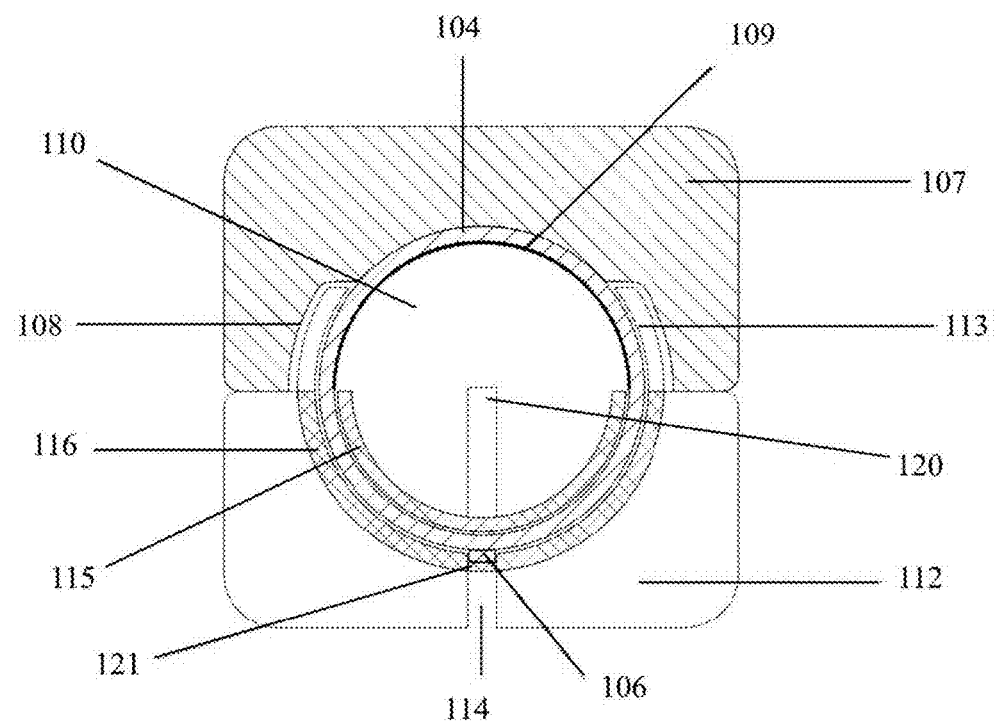
FIG. 2 is a cross section of the syringe in FIG. 1 taken at the level of cylinders handle.

FIG. 2 is a cross section of the Model (A) embodiment, where the cut is along the cylinders handle [107]. FIG. 2 shows the cylinder body [104] with the prominence [106] extending like a spine from the outer surface of the cylinder body [104]. The cylinder handle [107] in this embodiment is disposed at the rear end [110] of the hollow cylinder body, and extends radially over one half of the cylinder body [104], although in other embodiments the extension can be as small as 20% or as large as 80% about the hollow cylinder body [104]. An external surface of the cylinder handle [107] has sufficient surface area for a user to place all or part of his or her thumb so the user can apply a force from their thumb to the cylinder handle [107]. The cylinder handle [107] has grooves [108] formed therein that are arcuate in shape and match the front handle wings [113], although are larger than the front handle wings [113] so the front handle wings can pass through the grooves [108] without obstruction. The grooves [108] have the same curvature as the outer cylinder body [104]. Once again, the internal cylinder prominence [109] located at the rear (posterior) end of the cylinder reduces the risk of accidental removal of the plunger body while performing an aspiration operation. The front (anterior) plunger handle [112], the wings [113], the space between the external arms and front plunger handles [114] that allows the straight longitudinal prominence [106] to pass through it, an external plunger arms connecting piece [121] that is connects the external plungers arms [116] together and prevents them to deviate away from cylinder body [104], both internal [115] and external [116] plunger arms that cover, in this embodiment, one-half of the cylinder body, share similar arcuate curvature. The projection from the projection arm (or internal arm) [120] supports the seal [111] and prevents the seal from bending during injection or aspiration.

Figure 3:
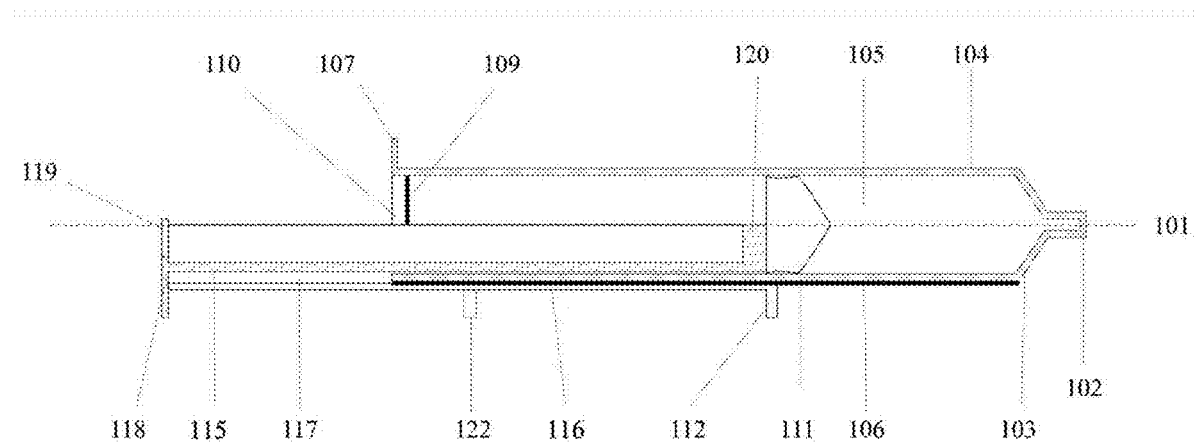
FIG. 3 is a longitudinal cross section of the syringe in FIG. 1 taken alone the syringe axis.

FIG. 3 is a longitudinal cross section of the embodiment of Model (A) and taken along the syringe axis [101]. FIG. 3 shows the cylinders body [104] that has cone like frontal tip [103] which terminates with the syringe tip [102] and is configured to have needles or tubes attached to it. The cylinders rear (posterior) end [110] where the cylinder handle [107] is disposed, is sized to receive the seal [111] into the cylinder cavity [105]. FIG. 3 also shows the straight longitudinal prominence [106] extending along the external surface of the cylinder. FIG. 3 also shows the internal cylinder prominence [109] positioned at the internal surface of rear cylinder body so as to decrease the incidence of accidental removal of plunger body while aspirating. The seal [111] which will be made either from the same material that the plungers parts made from or it will be covered by rubber material to prevent the sample to leak from the cylinder cavity [105] around the seal [111] when injecting and prevent the gas to pass through it to the sample that is contained in the cylinder cavity [105] while aspirating. The seal [111] is attached at its posterior surface with the front end of internal arm [115] and to its projection [120] that supports the seal [111] and prevents its bending while injecting or aspirating. The internal plunger arm [115] is adherent to the inner surface of the cylinder, and it is attached posteriorly to the anterior surface of the rear plunger handle [118] that is attached to the posterior end of the external plunger arms [116], too. The internal and external plungers arms have the gap [117] between them that is similar to the cylinders body [104] thickness to allow the passage of cylinder body [104] between plungers internal and external arms. The rear plunger handle [118] has a notch [119] nearly similar to the internal arm curvature, this notch is created to avoid the user's thumb from touching the plunger rear handle [118] when it is placed over the posterior surface of cylinder handle [107] while initiating the aspiration process. The additional plunger handle [122] can be added over the outer surface of the external plunger arms [116] if the syringe size is large; i.e. larger than the one hand's grip.

Figure 4:
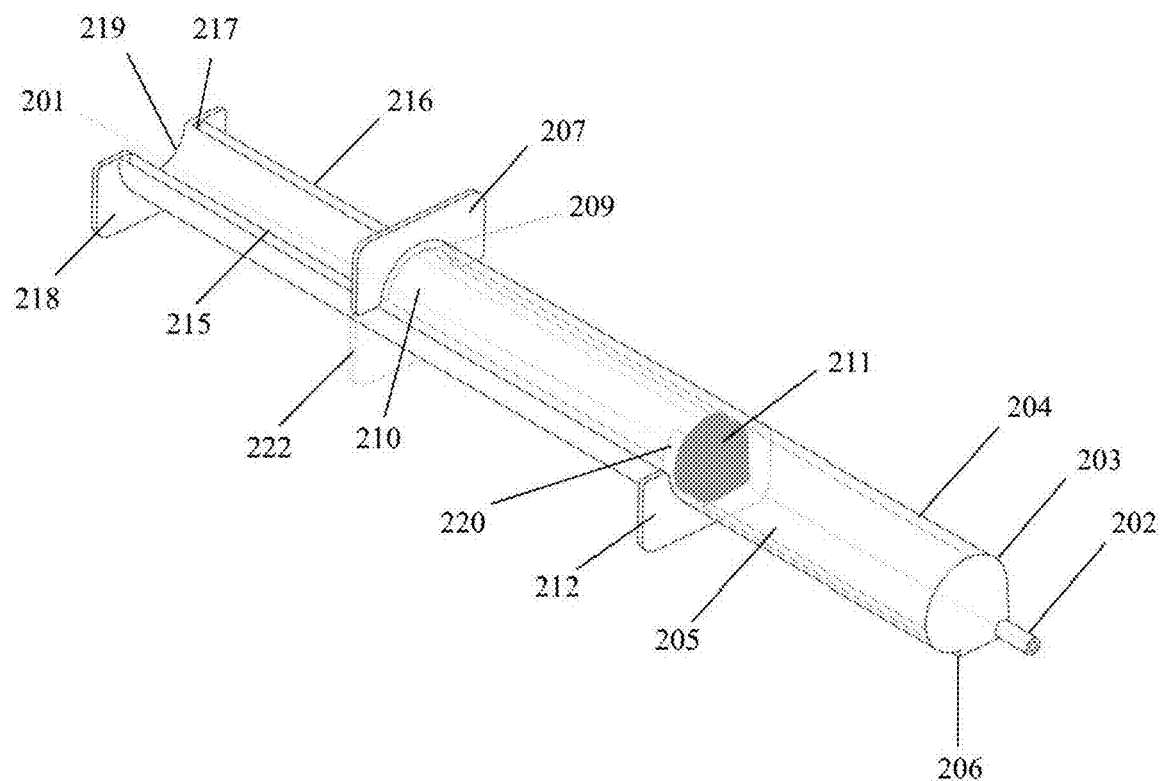
FIG. 4 is a perspective view of a syringe for one-handed injection and aspiration according to an embodiment B.
Figure 5:
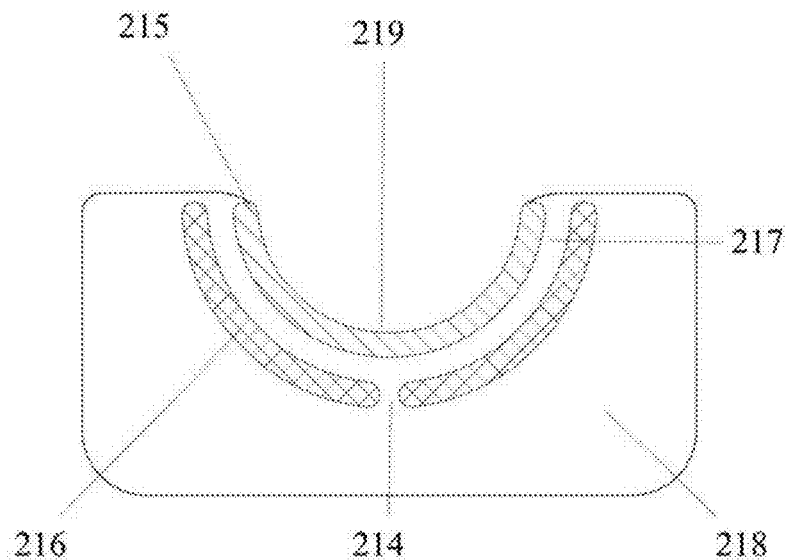
FIG. 5 is a cross section of the syringe in FIG. 4 taken at the level of cylinders handle.
Figure 6:
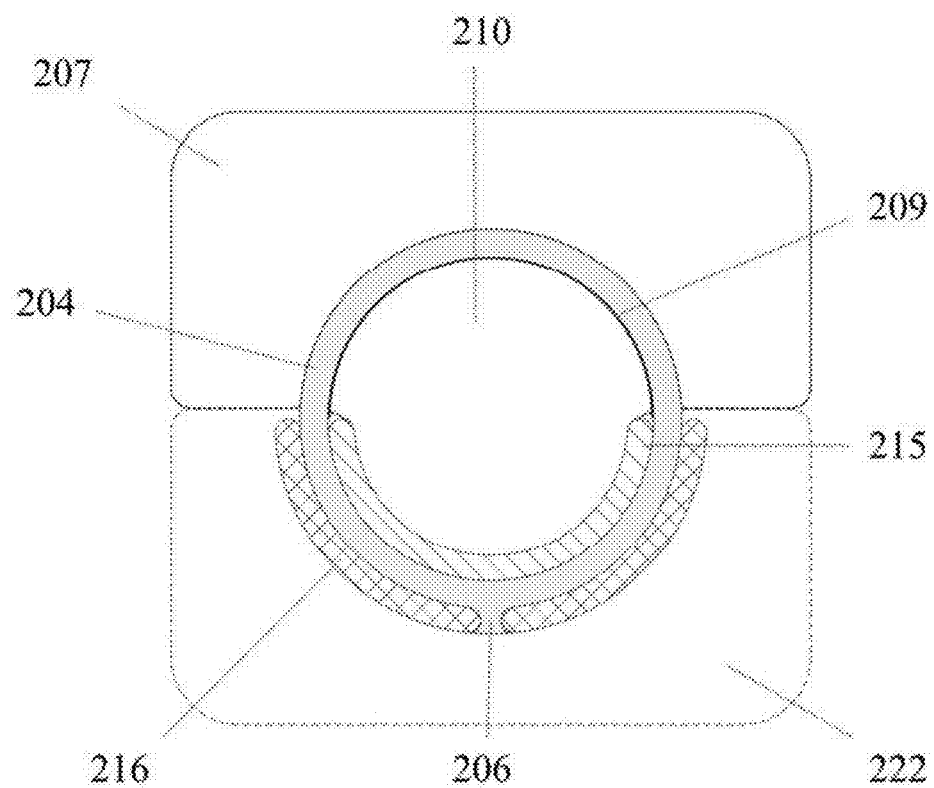
FIG. 6 is a cross section of the syringe in FIG. 4 taken at the level of cylinders cylinder handle.

The embodiment of Model (B) is illustrated by FIGS. 4, 5 & 6. It is composed of Cylinder which has the following components: [202], [203], [204], [205], [206], [207], [209] and [210], and Plunger body which has the following components: [211], [212], [214], [215], [216], [217], [218], [219], [220], [221] and [222]. Many of the features of this embodiment are similar to that previously described in the embodiment of Model (A), as shown in FIGS. 1-3, and therefore the detailed explanation will not be repeated, although the description is equally applicable.

FIG. 4 is a perspective view of model (B). The hollow cylinder has a cone-like front (anterior) end [203], which ends with the syringe tip (frontal tip) [202] that is configured to have needles or tubes attached to it. The cylinder's rear (posterior) end [210] is open to allow the seal [211] and internal plunger's arm [215] to pass therethrough and into the cylinder's cavity [205]. The cylinder handle [207] is disposed on the rear (posterior) cylinder end [210]. A straight longitudinal prominence [206] is created over the external surface of the cylinder body [204] confronting the cylinder handle [207] which passes through the space [214] and has two arcuate side surfaces that receive inner side edges of the external plunger arms. The snug fit of the arms in the prominence [206] permits the plunger's movement to be straight during injection/aspiration and prevents any spirally or rotational movement during use.

When the plunger body is pulled to a maximum displacement, the rear part of the seal [211] will stop when it reaches the internal prominence from cylinder body [209] which is found at the rear aspect of hollow cylinder [210]. This prominence [209] will eliminate the possibility of accidental removal of plunger body while aspirating. The plunger body is composed a seal [211] which is connected to the internal plunger arm [215]. The internal plunger arm [215] has a same curvature of the inner surface of cylinder body [204] and it moves axially adherent to it. To strengthen the seal [211], a projection from the internal arm [220] prevents its bending while injecting or aspirating. The rear end of internal plunger arm [215] is connected to the anterior surface of the rear (posterior) plunger handle [218], and it is positioned in one side of the syringe's axis [201]. The rear (posterior) plunger handle [218] has a notch [219] nearly similar to the internal arm curvature, and the handle anterior surface is attached the rear ends of internal plunger arm [215] and external plunger arms [216] which are shaped to be posited over one-half side of the cylinder body [204], and remain adherent to it. Moreover, they have similar curvature of inner and outer surfaces, respectively. There is a gap between the external and internal arms [217] that is similar to the cylinders body [204]thickness, and it allows the passage of cylinder body between plunger's internal and external arms. The front end of the external plunger arms [216] align with the rear surface of front plunger handle [212] and the seal [211]. The additional plunger handle [222] can be added over the outer surface of the external plunger arms [216] if the syringe size is large; i.e. larger than the one hand's grip.

FIG. 5 is a cross section of Model (B) taken at rear plunger's handle. FIG. 5 shows the external plunger's arms [216] and internal plunger's arm [215] arrangements. There is a gap between the external and internal arms [217] that is similar to the cylinders body thickness, and it allows the passage of cylinder body between plunger's internal and external arms. The external plunger's arms [216] have a space [214] between them to allow passage of the straight longitudinal prominence which has two arcuate surfaces to receive side surfaces of the plunger arms. Rear plunger handle [218] has a notch [219] nearly similar to the internal arm curvature. This notch [219] is created to avoid a users thumb from touching the plunger rear handle [218] when it is put over the posterior surface of cylinder handle while initiating the aspiration process.

FIG. 6 is a cross section taken at the rear cylinder's handle [207]. FIG. 6 shows the cylinder body [204] and its rear end [210]. The internal prominence extending from cylinder body [209] decreases the possibility of accidental removal of the plunger body while aspirating. FIG. 6 also shows how the external plunger's arms [216] are articulated to arcuate surfaces of the straight longitudinal prominence [206]. The external plunger's arms [216] and internal plunger's arm [215] cover one-half of the cylinder body. The additional plunger handle [222] can be added over the outer surface of the external plunger arms [216] if the syringe size is large; i.e. larger than the one hand's grip.

A device according to the present disclosure is easy to use with a one-handed grip while aspirating and injecting samples accurately and comfortably. The above-mentioned descriptions of the syringe parts and items are meant to illustrate, rather than to limit the scope of what has been disclosed. To the extent not otherwise disclosed, materials for the syringe may be the same as those used for conventional design. Moreover, while individual features of various figures may be shown in some drawings but not in others, skilled in the art will recognize that individual features of one embodiment are capable of being combined with any or all features of another embodiment. Thus, it is to be understood that the syringe is not limited in its application to the details of the descriptions set forth herein, or as illustrated in the drawings. Rather, it will be understood that the syringe is capable of being configured in other embodiments and of being practiced or of being carried out in various ways. It will also be understood that certain terminology used herein is for the purpose of description and should not be regarded as limiting. The use herein of "including," "containing," or "having" and variations of those words is meant to encompass the items listed thereafter, and equivalents of those, as well as additional items. The syringe has variable sizes, and it can be made from metals, glass or plastics. It can be used in many applications; as in medical field, laboratories, agriculture, and different industrial fields, etc. This syringe has a special design which facilitates using one hand either while aspirating the sample or injecting it.

To use the current syringe in aspiration, a hollow needle or tube is connected to the frontal tip [102] [202], and the user's forefinger(s) is then applied over the anterior surface of the plunger's front handle [112] [212] and the user's thumb over the posterior surface of the cylinders handle [107] [207]. By bringing the forefinger(s) and thumb toward each other, the plunger body with the seal [111][211] will move backward inside the cylinders cavity [105] [205], toward the cylinders rear end [110] [210], making a negative pressure inside the cylinders cavity [105] [205], which will cause the cylinder body to be filled-up with the aspirated sample that enters through the syringe tip [102] [202]. When the seal [111] [211] reaches the internal cylinder prominence [109] [209], there will be resistance to further movement of the seal [111] [211]. To inject the samples, a same hand can be used by applying the thumb over the posterior surface of the plunger's rear handle [118] [218] and forefinger(s) over the anterior surface of the cylinder's handle [107] [207]. By bringing the forefinger(s) and thumb toward each other, the plunger body with the seal [111] [211] will move forward, toward the cylinder's front end [103] [203], thereby injecting the sample out of the cylinders cavity [105] [205] through its tip [102] [202].

The issue of using large size syringes is solved with an additional handle(s) [122] [222] placed over the outer surface of the plunger's external arms [116] [216], and can be used in a two-step process. To aspirate the samples, the forefinger(s), first, are applied over the anterior surface of the additional plunger's handle [122][222] and thumb over the posterior surface of the cylinder's handle [107] [207]. By pinching the forefinger(s) and thumb toward each other, the plunger body with its seal [111] [112] will be pulled backward until the additional plunger's handle [112][222] and the cylinders handle [107] [207] are close to each other. Then, the forefinger(s) is(are) relocated and applied over the anterior surface of the plunger's front handle [112] [212], without moving the thumb from its place; i.e. over posterior surface of the cylinders handle [107] [207], and bringing the forefinger(s) and thumb toward each other again in a second step. This results in the plunger body with the seal [111] [211] continuing its rearward movement inside the cylinder's cavity [105] [205], toward the cylinder's rear end [110] [210], making a negative pressure inside the cylinder's cavity [105] [205]. In turn, the cavity is filled up with the aspirated sample that enters through the syringe tip. Once the seal [111] [211] reaches the internal cylinder prominence [109] [209], there will be resistance to the movement of seal [111] [211]. To inject samples with the presence of the additional plunger's handle [112] [222] is started with applying the thumb over the posterior surface of one of the additional plunger's handles [112][222], and the forefinger(s) over the anterior surface of the cylinder's handle cylinder's handle [107] [207]. Bringing the forefinger(s) and thumb toward each other, the plunger body with its seal [111] [112] will move halfway toward the cylinders front end [103] [203] until the additional plungers handle [112] [222] and the cylinders handle [107] [207] are close to each other. At this point, the thumb is relocated and placed against the posterior surface of the plungers rear handle [118] [218] without moving the forefinger(s) from the anterior surface of the cylinders handle [107] [207]. Once again, by bringing the forefinger(s) and thumb toward each other, the plunger body with the seal [111] [211] will continue its forward movement inside the cylinders cavity [105] [205], toward the cylinders front end [103] [203], injecting the remaining amount of the sample from the cylinder cavity [105] [205] through the syringe tip [102] [202]. To make the plunger movement straight and prevent its spiral rotation, a prominence [106] [206] is disposed along the outer surface of cylinder to guide the plunger as it is passing through the front plunger handle [112] [212] and between the external plunger arms [116] [216].

REFERENCE SIGNS LIST

101/201 Syringe Axis.
102/202 Frontal Tip.
103/203 Front Cylinder End.
104/204 Hollow Cylindrical Body.
105/205 Internal Opening of Hollow Cylinder Cavity.
106/206 Straight External Prominence
107/207 Cylinder Handle
108 Cylinder Handle's Groove
109/209 Internal Prominence from Cylinder Body
110/210 Cylinder Rear (Posterior) End
111/211 Seal
112/212 Front (Anterior) Plunger Handles
113/213 Wings of Front Plunger Handles
114/214 Space Between Plunger Arms and Handles
115/215 Internal Plunger Arms
116/216 External Plunger Arms
117/217 Gap Between Internal and External Arms
118/218 Rear (Posterior) Plunger Handle
119/219 Notch
120/220 Projection Arm
121 External Plunger Arms Connecting Piece
122/222 Additional Plunger Handle

The invention claimed is:

1. A hand-held aspiration syringe configured for one-handed operation, comprising:
 a plunger having
  a seal at a forward end thereof,
  a rear plunger handle at a rear end thereof,
  an internal plunger arm attached at a rear end thereof to the rear plunger handle and to the seal at a forward end thereof, an external plunger arm attached at a rear end thereof to the rear plunger handle and to a front plunger handle at a forward end thereof, the internal plunger arm being arranged co-axially with the external plunger arm and separated by a gap, and the front plunger handle extends radially away from the external plunger arm and has two portions separated by a space, the two portions each receive a different forefinger of a user, the front plunger handle and external plunger arm having the space; and a hollow cylindrical body having
- a wall with a thickness that matches the gap, at least a portion of the wall being disposed in the gap between the internal plunger arm and external plunger arm,
- a straight external prominence being a single prominence formed longitudinally along an outer surface of the hollow cylindrical body, an inner diameter of an internal opening of the hollow cylindrical body matches an outer diameter of the seal, the straight external prominence extending away from the outer surface of the hollow cylindrical body,
- a frontal tip formed at a forward end of the hollow cylindrical body through which fluid is drawn into an inner portion of the hollow cylindrical body in response to the seal being drawn away from the frontal tip, and
- a cylinder handle formed at a rear end of the hollow cylindrical body, wherein the space of the front plunger handle being formed in the front plunger handle and located between respective surfaces of the front plunger handle that receive the respective forefingers of the user,
- the space of the front plunger handle being sized to receive the straight external prominence therein such that when a rearward force is applied to a front side of the front plunger handle by the respective forefingers of the user, the force urges the front plunger handle and seal to move along the wall of the hollow cylindrical body and away from the frontal tip as guided by the straight external prominence.

2. The syringe according to claim 1, wherein
the front plunger handle is disposed on a same side of the hollow cylindrical body as the straight external prominence, and
the rear plunger handle is disposed on an opposite side of the hollow cylindrical body as the straight external prominence.

3. The syringe according to claim 2, further comprising:
an additional plunger handle is disposed on the same side of the hollow cylindrical body as the straight external prominence and positioned between the front plunger handle and the rear plunger handle.

4. The syringe according to claim 1, wherein the plunger further comprising:
a projection arm that contacts the seal and extends radially inward from the internal plunger arm toward a center of the hollow cylindrical body, and reinforces the seal of the plunger while a force is applied to at least one of the front plunger handle, the rear plunger handle, and cylinder handle.

5. The syringe according to claim 1, wherein
the front plunger handle comprising wings that extend at least partially around an outer surface of the hollow cylindrical body in opposing directions.

6. The syringe according to claim 5, wherein
the cylinder handle comprising spaces on opposing sides of the outer surface of the hollow cylindrical body that permit passage of the wings through the spaces while the front plunger handle is drawn past the cylinder handle during an aspiration operation where the plunger is at least partially withdrawn from the hollow cylindrical body.

7. The syringe according to claim 1, wherein
the rear plunger handle has a notch formed therein to form a void for a thumb of an operator when it is placed on the cylinder handle while the seal is positioned adjacent to the frontal tip and the rear plunger handle is positioned adjacent to the cylinder handle.

8. The syringe according to claim 1, wherein
the seal comprises a material that prevents gas and liquid leakage from an inner surface of the hollow cylindrical body around the seal.

9. The syringe according to claim 1, wherein
the straight external prominence is integrally formed as part of an outer surface of the hollow cylindrical body.

10. The syringe according to claim 9, wherein
a cross-section of the straight external prominence includes arcuate side surfaces into which edges of external plunger arms fit such that the arcuate surfaces of the straight external prominence hold the edges of external plunger arms while the external plunger arms are moved lative to the hollow cylindrical body.

11. The syringe according to claim 9, wherein
a cross-section of the front plunger handles showing a piece connecting the with external plunger arms preventing them to deviate away from the hollow cylindrical body.

* * * * *